United States Patent [19]

Kreighbaum et al.

[11] 4,044,150

[45] Aug. 23, 1977

[54] ANTIHYPERTENSIVE 4'-[1-HYDROXY-2-[(1-PHENOXY ETHYL)-AMINO]ETHYL]METHANESULFONANILIDE AND SALTS THEREOF AND THERAPEUTIC USE

[75] Inventors: William E. Kreighbaum; Herbert R. Roth, both of Evansville, Ind.

[73] Assignee: Mead Johnson & Company, Evansville, Ind.

[21] Appl. No.: 697,508

[22] Filed: June 18, 1976

[51] Int. Cl.$^2$ .................. A61K 31/18; C07C 143/72; C07C 143/84

[52] U.S. Cl. .............................. 424/321; 260/556 A; 260/556 AR

[58] Field of Search ................ 424/321; 260/556 AR, 260/556 A

[56] References Cited

U.S. PATENT DOCUMENTS 3,341,584  8/1967  Larsen et al. .................... 260/556

OTHER PUBLICATIONS

R. H. Uloth, et al., J. Med. Chem. 9, 88–97 (1966).

Primary Examiner—Albert T. Meyers
Assistant Examiner—Daren M. Stephens
Attorney, Agent, or Firm—Robert H. Uloth; Robert E. Carnahan

[57] ABSTRACT

The sulfonamidophenethanolamine 4'-[1-hydroxy-2-[(2-phenoxyethyl)amino]ethyl]methanesulfonanilide is an antihypertensive beta-adrenergic blocking agent selectively lowering blood pressure with minimal reduction of heart rate.

11 Claims, 2 Drawing Figures

ANTIHYPERTENSIVE 4'-[1-HYDROXY-2-[(1-PHENOXY ETHYL)-AMINO]ETHYL]METHANESULFONANILIDE AND SALTS THEREOF AND THERAPEUTIC USE

BACKGROUND AND SUMMARY OF THE INVENTION

The invention relates to a novel sulfonamidophenethanolamine having drug and bio-affecting properties. Specifically, the invention is concerned with 4'-[1-hydroxy-2-[(2-phenoxyethyl)amino]ethyl]methanesulfonanilide characterized by Formula I or a pharmaceutically acceptable acid addition or metal salt thereof, to pharmaceutical compositions containing same and to methods of producing and utilizing said sulfonamidophenethanolamine and compositions in treatment of hypertension.

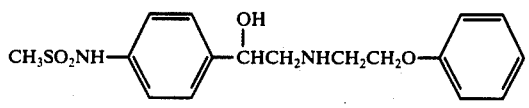

(I)

With respect to prior art relevant to the instant invention, A. A. Larsen, et al., U.S. Pat. No. 3,341,584 patented Sept. 12, 1967, discloses an extensive series of sulfonamidophenethanolamines and teaches that such compounds are useful as adrenergic alpha-receptor blocking agents or adrenergic beta-receptor blocking agents in addition to various other pharmacological utilities. The compound 4'-[1-hydroxy-2-[(1-phenoxyethyl)amino]ethyl]methanesulfonanilide is not, however, specifically disclosed in the Larsen, et al. patent. From a structural viewpoint, the instant compound (also referred to herein as Compound A) is homologously related to the prior art sulfonamidophenethanolamine "4-[2-(1-phenoxy-2-propylamino)-1-hydroxethyl]methanesulfonanilide." This compound, (also referred to herein as Compound B) is disclosed at column 11, Procedure 17, of the Larsen, et al. patent. According to R. H. Uloth, et al., J. Med. Chem. 9, 88–97 (1966), the aforesaid prior art compound (Compound B) is a beta-receptor blocking agent having four times the activity of dichloroisoproterenol in the isolated guinea pig tracheal spiral (see page 96, Compound 26 said reference.

Beta-adrenergic blocking agents are known to be of value in treating and controlling hypertension. They are also sometimes used in combination with an alpha-adrenergic blocking agent in preoperative management of patients with pheochromocytoma based on the rationale that beta-blockers may protect the heart from positive inotropic and chronotropic effects of high blood levels of circulating catechoamines. In the use of beta-adrenergic blocking agents in antihypertensive therapy, reduction of blood pressure is often accompanied by pronounced bradycardia (i.e. reduced heart rate). This is considered a serious side effect in that it generally contributes to exercise intolerance.

In the case of the aforesaid prior art sulfonamidophenethanolamine (Compound B) of U.S. Pat. No. 3,341,584, a substantial decrease in heart rate of mammals is elicited at effective antihypertensive or hypotensive doses whereas, surprisingly at effective antihypertensive or hypotensive doses, the compound of the instant invention elicits little or no significant change in heart rate.

DETAILED DESCRIPTION OF THE INVENTION

Figure 1:
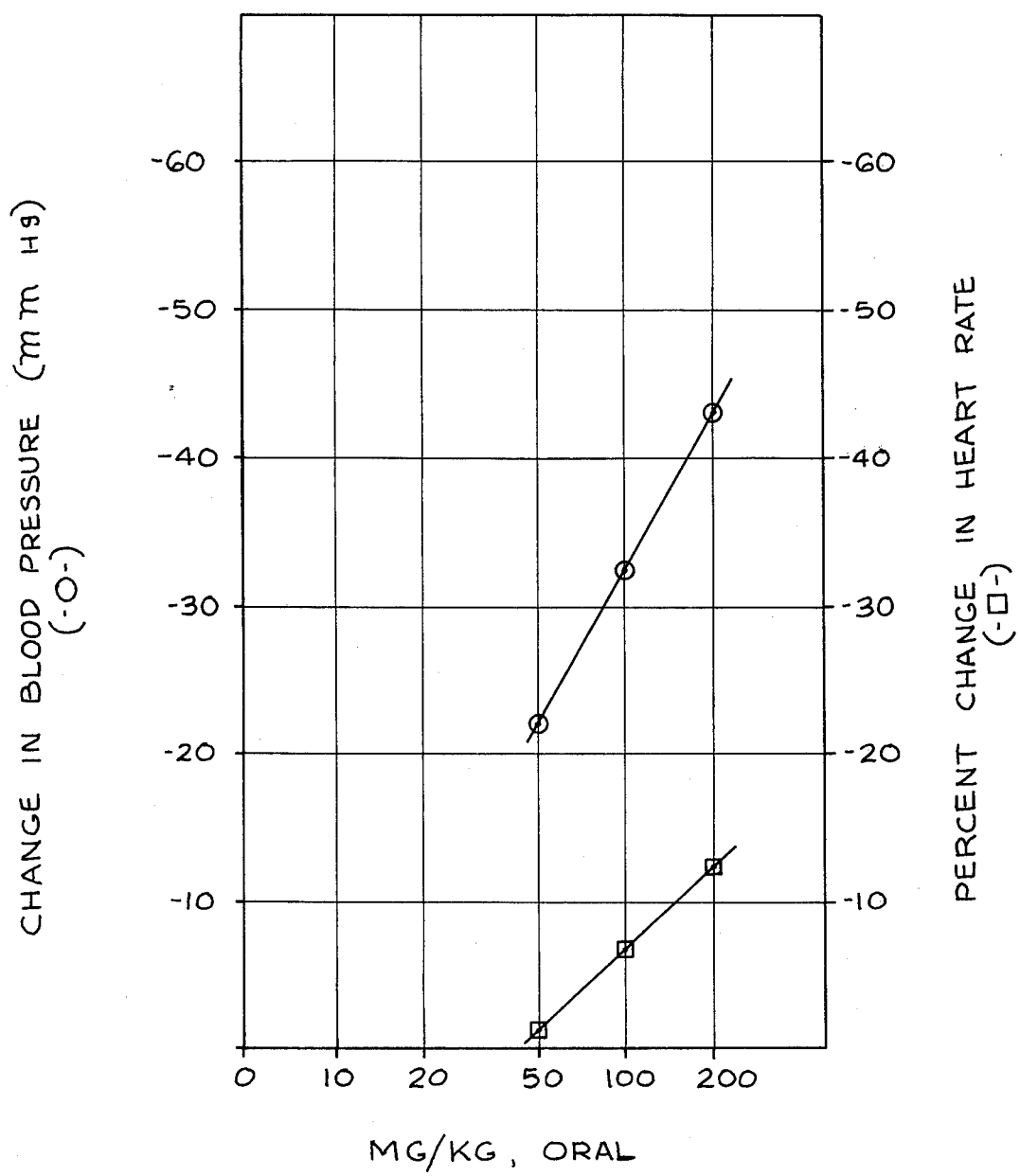
FIG. 1 constitutes a dose-response graph of blood pressure and heart rate changes determined in the spontaneous hypertensive rat 4 hours after orally administered 4'-[1-hydroxy-2-[(1-phenoxyethyl)amino]ethyl]methanesulfonanilide (Compound A). Blood pressure changes at doses of 50, 100, and 200 mg./kg. body weight are given in millimeters of mercury and are represented by circles (-0-) with percent change in heart rate represented by squares (-☐-).

It is to be understood that the term "pharmaceutically acceptable acid addition salt" used herein denotes a combination of 4'-[1-hydroxy-2-[(2-phenoxyethyl)amino]ethyl]methanesulfonanilide characterized by Formula I with a relatively non-toxic inorganic or organic acid. Illustrative of suitable acids which may be used are sulfuric, hydrochloric, phosphoric, hydrobromic, hydroiodic, sulfamic, methanesulfonic, benzenesulfonic, para-toluene sulfonic, acetic, lactic, succinic, maleic, mucic, tartaric, citric, gluconic, benzoic, cinnamic isethionic, fumaric, and related acids. Conversion of the instant compound to an acid addition salt is carried out by conventional methods as by interaction with an acid in an aqueous or non-aqueous medium. In a similar manner, treatment of the acid addition salt with a molar equivalent of an aqueous base solution (e.g., ammonium hydroxide, alkali metal hydroxides, alkali metal carbonates) result in a regeneration of the free base form.

It is to be understood that the term "pharmaceutically acceptable metal salt" used herein refers to a salt of the instant compound with metals such as sodium, potassium, calcium, magnesium, aluminum, and zinc. The metal salts are provided by neutralization of the acidic sulfonamido group with a molar equivalent of an alkali metal base.

The compound of Formula I possesses one asymmetric carbon atom in the CHOH- radical and therefore exists as a racemate as well as in the form of optical antipodes. The latter are obtained from the racemate by conventional resolution methods, for example, by salt formation of 4'-[1-hydroxy-2-[(2-phenoxyethyl)amino]ethyl]methanesulfonanilide racemate with an optically active acid, followed by fractional crystallization. It is to be understood that the stereo-isomeric forms of 4'-[1-hydroxy-2-[(2-phenoxyethyl)amino]ethyl]methanesulfonanilide are within the purview of the instant invention.

According to the present invention, the compound of Formula I is prepared by reducing 4'-[N-(2-phenoxyethyl)glycyl]methanesulfonanilide in a reaction inert solvent. Reduction is carried out catalytically, e.g. with nobel metal catalyst such as palladium-on-carbon, or by chemical reduction, e.g. with reagents such as sodium borohydride or borane, according to standard procedures, refer to Larsen, et al., U.S. Pat. No. 3,341,584, and Uloth, et al. J. Med. Chem. 9, 88–97 (1966).

The compound of Formula I as the hydrochloride is a relatively non-toxic substance having an oral $LD_{50}$ in mice of 1922 mg./kg. body weight and an intraperitoneal $LD_{50}$ of 273 mg./kg. body weight. In the female and male rat, the oral $LD_{50}$ is 1952 mg./kg. and 3552 mg./kg. body weight, respectively.

As stated hereinabove, an effective dose of the compound of the instant invention (Compound A) reduces blood pressure in mammals with little or no effect on heart rate. Conventional pharmacological tests measuring beta-adrenergic blocking activity and selectivity can be employed to illustrate that Compound A selectively reduces blood pressure with minor heart rate effects.

One such test involves the measurement of inherent cardiac and blood pressure effects in the isoproterenol challenged intact anesthetized dog. In this test model, dogs are anesthetized with a mixture of phenobarbital sodium (15 mg./kg.) and barbital sodium (225 mg./kg.) intravenously and are vagotomized bilaterally. Heart rate, contractile force and diastolic blood pressure are continuously recorded with alterations in these responses (e.g. tachycardia) produced by intravenously administered isoproterenol determined before and after injection of increasing doses of the test compound. The test substance is administered to separate groups of dogs at cumulative doses of 0.1, 0.3, 1, 3, and 10 mg./kg. body weight with each dose of the test substance infused slowly over a period of 3–5 minutes. After completing infusion of the test substance, a 10-minute equilibrium period is allowed for drug-receptor interaction and stabilization of the cardiovascular system before a series of isoproterenol challenges is initiated. Maximum response to isoproterenol is achieved after each dose of the beta-adrenergic blocking agent by logarithmically increasing the dose of this agonist as receptor blockade develops. Each dose of isoproterenol is given approximately 5 minutes after the previous one and the overall dose range for isoproterenol is from 0.03–300 micrograms per kilogram body weight. Mean changes in the resting levels of the cardiovascular variables (heart rate, contractile force, and mean arterial blood pressure) due to the administration of each agent (which is taken as a measure of the inherent drug effect) is determined and statistically compared using the Student's test. Results obtained for Compound A and Compound B are recorded in Table I.

Table I

Comparison of Inherent Cardiac Effects of 4'-[1-Hydroxy-2-[(2-phenoxyethyl)amino]ethyl]methanesulfonanilide (Compound A) and 4-[2-(1-Phenoxy-2-propylamino)-1-hydroxyethyl] methane sulfonanilide (Compound B) on Contractile Force (CF), Heart Rate (HR), and Mean Arterial Blood Pressure (MABP) in the Anesthetized Dog Challenged with Isoproterenol

| Drug | Dose (mg/kg, i.v.) | CF (gm) | HR (bpm)[a] | MABP (mm Hg) |
|---|---|---|---|---|
|  |  | (110 ± 4)[b] | (149 ± 8)[b] | (105 ± 7)[b] |
| Compound A | 0.1 | 9 ± 6 | 18 ± 4 | 11 ± 1 |
| (4 dogs) | 0.3 | 8 ± 6 | 22 ± 4 | 17 ± 3 |
|  | 1.0 | 11 ± 5 | 32 ± 5 | 12 ± 3 |
|  | 3.0 | 11 ± 5 | 38 ± 6 | 16 ± 4 |
|  | 10.0 | 17 ± 7 | 38 ± 6 | 34 ± 7 |
|  |  | (95 ± 8)[b] | (164 ± 7)[b] | (108 ± 8)[b] |
| Compound B | 0.3 | 6 ± 7 | 29 ± 6 | +1 ± 5[c] |
| (6 dogs) | 1.0 | 4 ± 7 | 39 ± 7 | 2 ± 6 |
|  | 3.0 | 4 ± 7 | 54 ± 7 | 10 ± 8 |
|  | 10.0 | 6 ± 9 | 72 ± 9 | 28 ± 14 |

[a]Beats per minute.
[b]Basal (control values).
[c]Increase from control rather than decrease.

It is clearly evident from Table I that Compound A provides a significant reduction of mean arterial blood pressure (11 ± 1 mm Hg) at a dose of 0.1 mg./kg. body weight with only a 12% reduction in heart rate. In comparison, a dose of 3 mg./kg. body weight of Compound B is required to provide an approximate equivalent reduction of arterial blood pressure with concomitant 33% reduction in heart rate. Furthermore, Compound A is distinguished from Compound B in that at doses in the range of 0.3 to 1.0 mg./kg. body weight Compound A effectively reduces mean arterial blood pressure whereas Compound B has no significant effect on this variable yet produces pronounced bradycardia.

Figure 2:
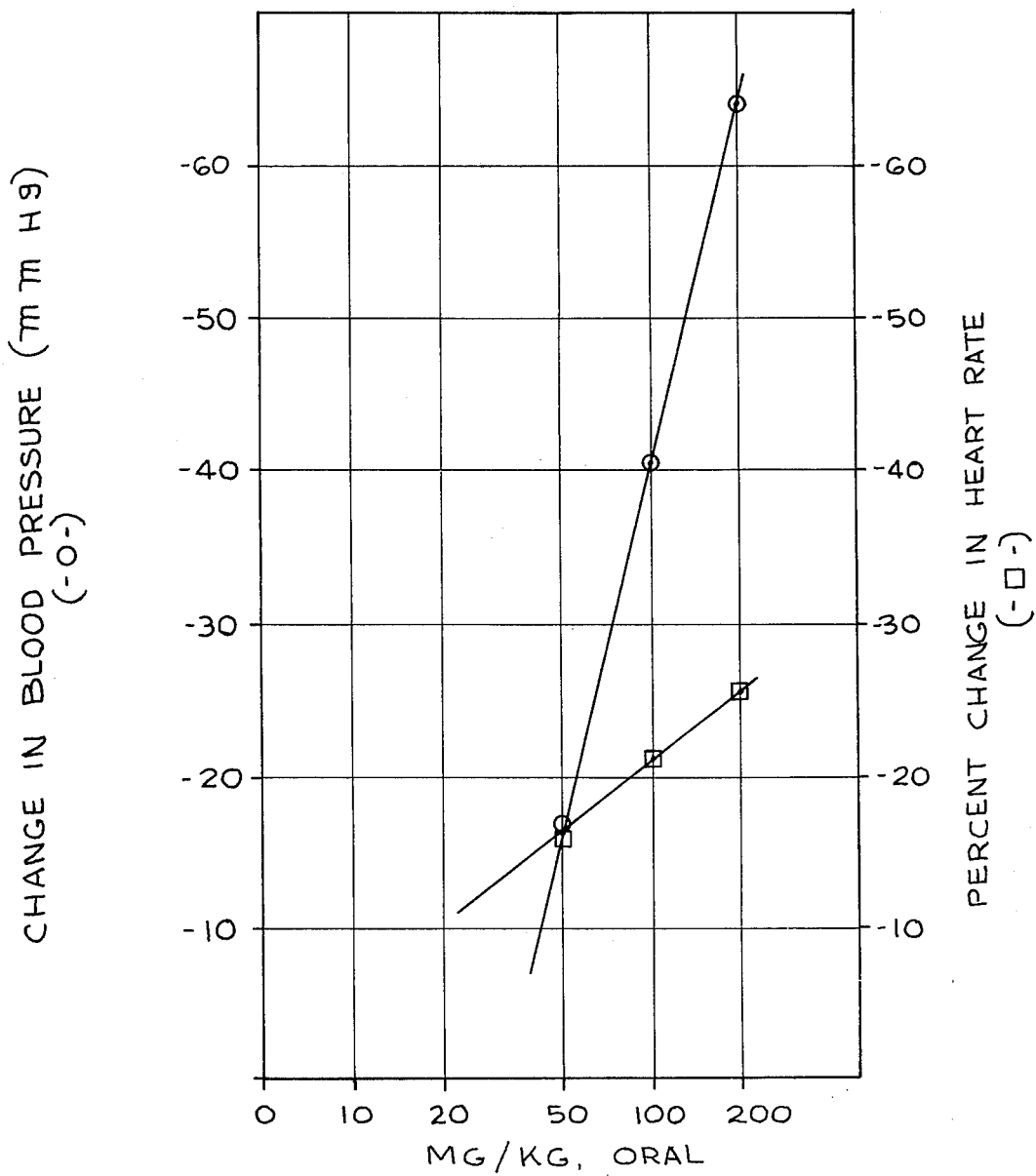
FIG. 2 constitutes a dose-response graph of blood pressure and heart rate changes similar to that of FIG. 1 for 4-[2-(1-phenoxy-2-propylamino)-1-hydroxyethyl]methanesulfonanilide (Compound B).

Another in vivo animal experiment considered predictive of antihypertensive utility by those skilled in the art is the lowering of blood pressure in an inbred strain of spontaneously hypertensive rat (SHR) established by Okamoto and Aoki. In this test, systolic blood pressure and heart rate determinations are made immediately before the animals are orally dosed to provide control values and subsequently thereafter at 4 and 24-hour periods to determine drug effect. Various doses of test drug are administered and a dose-response graph obtained by plotting (on semi-log paper) the observed change (mm Hg) in systolic blood pressure and percent change in heart rate as absciscas against the dose as the ordinate. FIG. 1 provides dose-response graph of blood pressure and heart rate effects of orally administered Compound A at doses of 50, 100, and 200 mg./kg. body weight, and FIG. 2 constitutes similar graphs for prior art Compound B. FIG. 1 illustrates that doses of 50–200 mg. of Compound A reduces blood pressure by 22–43 mm Hg with minimal reduction of heart rate of from 2–12%. FIG. 2 illustrates that comparable doses of Compound B reduces systolic blood pressure by 18–64 mm Hg but with pronounced bradycardia ranging from 17–25%. Values set forth in Table II below are taken from FIGS. 1 and 2.

Table II

Comparison of Antihypertensive Activity of 4'-[1-hydroxy-2-[(2-phenoxyethyl)amino]ethyl]methanesulfonanilide (Compound A) and 4-[2-(1-phenoxy-2-propylamino)-1-hydroxyethyl] methanesulfonanilide (Compound B) in the Spontaneous Hypertensive Rat

|  | Compound A | Compound B |
|---|---|---|
| Dose (mg./kg. body weight) which lowers blood pressure by 40 mm Hg | 165 | 100 |
| Percent decrease in heart rate at dose lowering blood pressure by 40 mm Hg | 11% | 21% |
| Dose (mg./kg. body weight) which lowers heart rate by 10% | 150 | 18 |
| Percent decrease in blood pressure at dose lowering heart rate by 10% | 38% | no significant reduction |

It is evident from Table II that at doses sufficient to reduce blood pressure by 40 mm Hg, Compound A has only about 50% of the bradycardia liability of Compound B. In clinical practice a 10% reduction in heart rate is reasonably tolerated in most patients with hypertension whereas reduction of 20% or more is often associated with problems such as exercise intolerance. Thus, the results regarding decrease in blood pressure at doses lowering heart rate by 10% are of particular importance in distinguishing Compound A from the prior art Compound B. At a dose reducing heart rate by 10%, Compound A provides 38% reduction in blood pressure whereas, surprisingly, Compound B has no effect on blood pressure.

The antihypertensive process of the instant invention comprises systemically administering to a mammal having hypertension or predisposed thereto an effective antihypertensive amount of a compound selected from the group consisting of 40'-[1-hydroxy-2-[(2-phenoxyethyl)amino]ethyl]methanesulfonanilide or a pharmaceutically acceptable acid addition salt or metal salt thereof. By systemic administration, it is intended to include both oral and parenteral routes with the oral route particularly preferred from a convenience viewpoint. Examples of parenteral administration are intramuscular, intravenous, intraperitoneal, rectal, and subcutaneous administration. Dosage will vary according to form of administration with from about 0.05 to 15 mg./kg. body weight of 4'-[1-hydroxy-2-[(2-phenoxy)amino]-ethyl]methanesulfonanilide administered in effective single or multiple dosage units generally providing the desired antihypertensive effect. When administered orally, a dose of 0.5 mg./kg. to 15 mg./kg. body weight is preferred.

The compound of the instant invention characterized by Formula I either as the free base or as the pharmaceutically acceptable acid addition salt or metal salt thereof in combination with a pharmaceutical acceptable carrier may be administered in the antihypertensive process of the instant invention. The carrier may be a solid, semisolid, or liquid diluent. These pharmaceutical preparations constitute another aspect of the invention.

In the preparation of pharmaceutical compositions containing the compound of Formula I in the form of dosage units for oral administration, the compound is mixed with a solid, pulverulent carrier, as e.g. with lactose, saccharose, sorbitol, mannitol, starch, as potato starch, corn starch, amylopectin, cellulose derivatives, or gelatin, as well as with glidents such as magnesium stearate, calcium stearate, polyethylene glycol waxes or the like and pressed into tablets. The tablets may be used uncoated or coated by known techniques to delay disintegration and adsorption in the gastrointestinal tract and thereby provide a sustained action over a longer period. When coated tablets are wanted, the above prepared core may be coated with concentration solution of sugar, which solution may contain e.g. gum arabic gelatin, talc, titanium dioxide or the like. Furthermore, the tablets may be coated with a lacquer dissolved in an easily volatile organic solvent or mixture of solvents and if desired, dye may be added to this coating.

In the preparation of soft gelation capsules consisting of gelation and e.g. glycerine and the like the active ingredient is mixed with a vegatable oil. Hard gelatin capsules may contain granules of the active ingredient in combination with a solid, pulverulent carrier such as lactose, saccharose, sorbitol mannitol, starch (such as e.g. potato starch, corn starch or amylopectin), cellulose derivatives or gelatin.

Dose units for rectal administration may be prepared in the form of suppositories containing the compound in a mixture with a neutral fat base, or in the form of a gelatin-rectal capsule with a mixture of vegetable oil or parafin oil.

Liquid preparations of Compound A suitable for oral administration are suspension, syrups and elixirs containing from about 0.2% by weight to about 75% by weight of the active ingredient alone or admixed with an inert solid diluent such as calcium carbonate, calcium phosphate, kaolin, and the like.

A suitable injectible composition of Compound A comprises an aqueous solution of the hydrochloride salt adjusted to physiologically acceptable pH.

The invention is illustrated but not limited by the following examples.

EXAMPLE 1

4'-[1-Hydroxy-2-[(2-phenoxyethyl)amino]-ethyl]methanesulfonanilide Hydrochloride a. 4'-[N-(2-phenoxyethyl)glycyl]methanesulfonanilide Hydrochloride To a stirred solution of phenoxyethylamine (137 g., 1.0 mole) and triethylamine (101 g., 1.0 mole) in 3.4 liter of acetonitrile is added p-chloroacetylmethanesulfonanilide (247.7 g., 1.0 mole) in portions over a period of 0.5 hr. while maintaining a temperature of 35° C. The reaction mixture is warmed to about 70° C. over a period of 0.5 hr., then held at a temperature of 70°–75° C. for 1.0 hr. and cooled in an ice bath. Insolubles are collected, washed with 150 ml. of cold acetonitrile and air dried affording 193 g. of material. This material is suspended in 900 ml. of hot methanol and acidified with 75–80 ml. of a solution of 4.7 N ethanolhydrochloric acid with stirring. The mixture is cooled, insolubles collected, washed with 50 ml. of cold methanol and air dried to afford 128 g. of the hydrochloride salt of 4'-[N-(2-phenoxyethyl)glycyl]-methanesulfonanilide, m.p. 223°–227° C. (dec.).

The mother liquid from the filtration is further acidified with ethanol-hydrochloric acid to a pH of about 4–5 and the resulting precipitate collected, washed with acetonitrile, and triturated with hot methanol to yield an addition 16.6 g. of 4'-[N-(2-phenoxyethyl)-glycyl]-methanesulfonanilide hydrochloride, m.p. 219°–222° C.

b. 4'-[1-Hydroxy-2-[(2-phenoxyethyl)amino]ethyl]methanesulfonanilide Hydrochloride To a suspension of 40'-[N-(2-phenoxyethyl)-glycyl]-methanesulfonanilide hydrochloride (77.0 g., 0.2 mole) in 1 liter of hot methanol is added 7.7 g. of 10% palladium-on-carbon catalyst suspended in 200 ml. of methanol. The mixture is hydrogenated on a Parr hydrogenation apparatus at 50 psi hydrogen pressure at a temperature of 50° C. for a period of 24 hrs. or until no further uptake of hydrogen is observed. The warm reaction mixture is filtered and the filtrate concentrated under reduced pressure to a solid residue. Trituration of the residue with 1:1 isopropanol-isopropyl ether affords 71.4 g. of off-white solid, m.p. 192°–194° C. (dec.). Crystallization of this material from methanol-isopropyl ether affords analytically pure 4'-[1-Hydroxy-2-[2-phenoxyethyl)amino]ethyl]methanesulfonanilide hydrochloride in a yield of 81.6%, m.p. 193.0°–194.5° C. (dec.) (corr.).

Analysis: Calcd. for $C_{17}H_{22}N_2O_4S \cdot HCL$ (percent): C, 52.77; H, 5.99; N, 7.24. Found (percent): C, 52.89; H, 6.01; N, 7.20.

Nuclear magnetic resonsance, DMSO-$d_6$ with tetramethylsilane as reference, $\delta$(ppm) (multiplicity, relative area): 3.00 (s,3); 3.35 (m,4); 4.39 (t, 6.0 Hz, 2); 5.08 (m,1); 6.26 (bs,1); 7.30 (m,9); 9.45 (bs,2); 9.90 (bs,1).

Neutralization of an aqueous solution of the hydrochloride salt with ammonium hydroxide affords 4'-[1-hydroxy-2-[(2-phenoxyethyl)-amino]ethyl]methanesulfonilide free base on an insoluble solid, m.p. 142°–144° C. (corr.).

Analysis. Calcd. for $C_{17}H_{22}N_2O_4S$ (percent): C, 58.26; H, 6.33; N, 8.00. Found (percent): C, 58.38; H, 6.40; N, 7.86.

c.
4'-[1-Hydroxy-2-[(2-phenoxyethyl)amino]ethyl]methaneslfonanilide Sodium Salt A solution of sodium methoxide prepared from sodium (0.23 g., 0.01 gram atom) and 15 ml. of methanol is mixed with a solution of 4'-[1-hydroxy-2-[(2-phenoxyethyl)amino]ethyl]methanesulfonanilide (3.5 g., 0.01 mole) in 50 ml. of methanol. Anhydrous ether is added to precipitate the sodium salt or the methanolic solution is concentrated under reduced pressure to provide 4'-[1-hydroxy-2-[(2-phenoxyethyl)amino]ethyl]methanesulfonanilide sodium salt.

Other metal salts such as potassium, lithium and aluminum may be prepared by substituting the appropriate base for sodium methoxide in the foregoing example or by reacting the sodium salt of 4'-[1-hydroxy-2-[(2-phenoxyethyl)amino]ethyl]methanesulfonanilide with a metal such as magnesium chloride, calcium chloride, barium chloride, or zinc chloride in an appropriate solvent allowing either for precipitation of the desired salt or precipitation of sodium chloride byproduct with retention of the desired salt in the solution.

EXAMPLE 2

Tablets

The following ingredients are blended in the proportion by weight indicated according to conventional pharmaceutical techniques to provide a tablet base.

| Ingredient | Amount |
| --- | --- |
| Lactose | 83 |
| Corn starch | 10 |
| Talcum | 2 |
| Gelatin | 4 |
| Magnesium stearate | 1 |

An appropriate amount of this tablet base is blended with sufficient 4'-[1-hydroxy-2-[(2-phenoxyethyl)amino]ethyl]methanesulfonanilide or a pharmaceutically acceptable acid addition salt or metal salt thereof to provide tablets containing 10, 20, 40, 80, 160 and 320 mg. of active ingredient. The tablets are formed in a conventional tablet press and preferably have a total weight of 200–600 mg. depending upon the amount of active ingredient.

EXAMPLE 3

Dry Filled Capsules

The following ingredients are blended in a conventional manner in the proportion by weight indicated.

| Ingredient | Amount |
| --- | --- |
| Lactose, U.S.P. | 50 |
| Starch | 5 |
| Magnesium stearate | 2 |

Sufficient 4'-[1-hydroxy-2-[(2-phenoxyethyl)amino]ethyl]methanesulfonanilide or a pharmaceutically acceptable acid addition salt or metal salt thereof is added to an appropriate amount of the blend to provide capsules containing 10, 20, 40, 80, 160, and 320 mg. of active ingredient (filled into hard gelatin capsules of a suitable size).

EXAMPLE 4

Suspensions

A suspension of 4'-[1-hydroxy-2-[(2-phenoxyethyl)amino]ethyl]methanesulfonanilide or a pharmaceutically acceptable acid salt or metal salt thereof is prepared with the following ingredients.

| Ingredient | Amount |
| --- | --- |
| Active ingredient | 20 g. |
| Sucrose, U.S.P. | 400 g. |
| Sorbitol, U.S.P. | 100 g. |
| Bentonite | 20 g. |
| Flavors, q.s. | |
| Water, q.s. to make 1 liter | |

Each milliliter of the suspension contains approximately 20 mg. of the active ingredient.

What is claimed is:

1. A compound selected from the group consisting of 4'-[1-hydroxy-2-[(2-phenoxyethyl)amino]ethyl]methanesulfonanilide and the pharmaceutically acceptable acid addition and metal salts thereof.

2. The compound defined in claim 1 which is 4'-[1-hydroxy-2-[(2-phenoxyethyl)amino]ethyl]methanesulfonanilide.

3. The compound defined in claim 1 which is 4'-[1-hydroxy-2-[(2-phenoxyethyl)amino]ethyl]methanesulfonanilide hydrochloride.

4. The compound defined in claim 1 which is 4'-[1-hydroxy-2-[(2-phenoxyethyl)amino]ethyl]methanesulfonanilide sodium salt.

5. An antihypertensive process which comprises systemically administering to a hypertensive mammal an effective antihypertensive amount of a compound selected from the group consisting of 4'-[1-hydroxy-2-[(2-phenoxyethyl)amino]ethyl]methanesulfonanilide and pharmaceutically acceptable acid addition and metal salts thereof.

6. The process of claim 5 wherein said compound is 4'-[1-hydroxy-2-[(2-phenoxyethyl)amino]ethyl]methanesulfonanilide.

7. The process of claim 5 wherein said compound is 4'-[1-hydroxy-2-[(2-phenoxyethyl)amino]ethyl]methanesulfonanilide hydrochloride.

8. The process of claim 5 wherein said effective dose is from 0.05 to 15 mg./kg. body weight of said mammal.

9. A pharmaceutical dosage unit adapted for systemic administration to a hypertensive mammal comprising a pharmaceutical carrier and an effective antihypertensive amount of a compound selected from the group consisting of 4'-[1-hydroxy-2-[(2-phenoxyethyl)amino]ethyl]methanesulfonanilide and pharmaceutically acceptable acid addition and metal salts thereof.

10. The composition of claim 9 wherein said compound is 4'-[1-hydroxy-2-[(2-phenoxyethyl)amino]ethyl]methanesulfonanilide.

11. The composition of claim 9 wherein said compound is 4'-[1-hydroxy-2-[(2-phenoxyethyl)amino]ethyl]methanesulfonanilide hydrochloride.

* * * * *